(12) United States Patent
Alemi et al.

(10) Patent No.: US 6,171,791 B1
(45) Date of Patent: Jan. 9, 2001

(54) NUCLEOTIDE SEQUENCE TYPICAL FOR A DELETION OF PROTO-ONCOGENE RET IN EXON 11

(75) Inventors: Mansour Alemi; Jan Sällström; Erik Wilander, all of Uppsala (SE)

(73) Assignee: Karyogene AB, Uppsla (SE)

( * ) Notice: Under 35 U.S.C. 154(b), the term of this patent shall be extended for 0 days.

(21) Appl. No.: 09/117,308

(22) PCT Filed: Feb. 14, 1997

(86) PCT No.: PCT/SE97/00245

§ 371 Date: Nov. 13, 1998

§ 102(e) Date: Nov. 13, 1998

(87) PCT Pub. No.: WO97/30086

PCT Pub. Date: Aug. 21, 1997

(30) Foreign Application Priority Data

Feb. 15, 1996 (SE) .................................................. 9600595

(51) Int. Cl.⁷ .............................. C07H 21/04; C12Q 1/68; C12P 19/34
(52) U.S. Cl. ........................... 435/6; 536/24.3; 536/24.31; 536/23.1; 435/91.2
(58) Field of Search ...................... 435/6, 91.2; 536/24.3, 536/24.31, 23.1

(56) References Cited

PUBLICATIONS

Alemi et al. Anticancer Research 16:2619–2622 (1996).*

* cited by examiner

*Primary Examiner*—Jeffrey Fredman
*Assistant Examiner*—Juliet C-Einsmann
(74) *Attorney, Agent, or Firm*—John Lezdey & Assoc

(57) ABSTRACT

An isolated and purified nucleic acid comprising a nucleotide sequence which consists of GAT CCA CTG TGC GAC AGC TCG GRG ATC (Seq. Id. No. 1) included in the proto-oncogene RET, which sequence in normal cells has the following sequence in the region defined by position 1810 and adjacent nucleotides including position 1845 and adjacent nucleotides: GAT CCA CTG TGC GAC GAG CTG TGC CGC ACG GTG ATC. Information derived from the altered nucleotide sequence found in a tissue or fluid sample, taken from a patient, can be used for determining the type and character of the rumor. The nucleotide sequence or information derived therefrom is used for the manufacture of reagents for the diagnosing of cancer and for the manufacture of pharmaceutical compositions for prevention and/or treatment of cancer.

8 Claims, 4 Drawing Sheets

Fig. 3

```
      627 628 629 630 631 632 633 634 635 636 637 638
5'    GAT CCA CTG TGC GAC GAG CTG TGC CGC ACG GTG ATC 3'

5'    GAT CCA CTG TGC GAC*AGC T*******CG GTG ATC 3'

A.

B.

NUCLEOTIDE SEQUENCE TYPICAL FOR A DELETION OF PROTO-ONCOGENE RET IN EXON 11

FIELD OF THE INVENTION

The present invention concerns a novel nucleotide sequence and methods for its use. In particular, the present invention concerns a novel nucleotide sequence which can be used in the diagnosis and treatment of cancer in mammals, in the production of reagents and kits for analysis and pharmaceutical compositions for treatment and/or prevention.

BACKGROUND OF THE INVENTION

Genetic alterations are associated with the genesis of neoplasia and could hence function as markers for early diagnosis of cancer. In all treatment of cancer, regardless of the method of therapy, the ability to identify cancerous tissue and cells is of uttermost importance. The need for substances, specifically binding to cancerous cells is also apparent. Further, the possibility of neutralizing or counteracting said alterations is a key to future prevention and treatment of cancer. Substantive research has been conducted to identify the specific alterations associated with different types of cancer. Only the knowledge of the specific alteration or alterations behind each type of cancer makes possible the use of selective methods in diagnosing, prevention and/or treatment.

PRIOR ART

The RET proto-oncogene encodes a transmembrane receptor tyrosine kinase, whose ligand has recently been identified as glial cell line-derived neurotrophic factor (GDNF) (Durbec et al., 1996; Trupp et al., 1996). Four hereditary diseases with autosomal dominant inheritance have been tied to mutations in the RET gene: familial medullary carcinoma (FMTC) (Farndon et al., 1986; Jackson and Norum, 1989; Lairmore and Wells, 1993); multiple endocrine neoplasia type 2A (MEN 2A) in which patients develop medullary thyroid carcinoma (MTC) and pheochromocytoma, (Sipple, 1961); MEN 2B which shows these two tumors in conjunction with skeletal abnormalities and ganglioneuromas of the gastrointestinal tract (Carney et al., 1976; Schimke et al., 1968), and Hirschprung's disease, shows a congenital lack of enteric plexus neurons resulting in intestinal immobility. In FMTC, germ-line point mutations are found in exons 10, 11, 13, 14 and 16 of the RET proto-oncogene (Bolino et al., 1995; Donis-Keller et al., 1993; Eng et al., 1995; Schuffenecker et al., 1994).

Point mutations in exons 10 and 11 have been reported in association with MEN 2A, while specific missense mutations in exon 16 have been found in MEN 2B and a small proportion of sporadic MTC (Donis-Keller et al., 1993; Eng et al., 1995; Hofstra et al., 1994; Mulligan et al., 1993). In addition, the deletion of six bases removing a cysteine at codon 630 or 634 has been reported in two separate cases of sporadic MTC. (S. Dou and H. Donis-Keller, unpublished results, (Kimura et al., 1995).

SUMMARY OF THE INVENTION

The present inventors have found, that specific deletions are indicative of cancer in cells of neural crest origin and that a specific, previously unknown deletion of nine base pairs in RET exon 11 is indicative of cancer in cells of neural crest origin, e.g. multiple endocrine neoplasia (MEN) type 2A and 2B, pheochromocytoma, enteric ganglioneuromatosis, parathyroid hyperplasia, ganglioneuromas and medullary thyroid cancer (MTC). The present inventors have succeeded in isolating and identifying this deletion and shown its relevance as a specific marker of medullary thyroid cancer. The scope of the invention will be apparent from the claims and the description and examples, which are to be read in connection with the appended figures.

BRIEF DESCRIPTION OF THE FIGURES

FIG. 3 shows partial sequences of normal RET exon 11 and the mutant as determined by DNA sequencing of the PCR product. Deleted bases are represented by asterisks, codon numbers are shown above and below the sequences, FIG. 4 A) shows the DNA environment immediately surrounding the 9 bp complex deletion and FIG. 4 B) shows the proposed hairpin loop created by the inperfect palindrome surrounding the deleted bases (asterisks).

DESCRIPTION OF THE INVENTION AND PREFERRED EMBODIMENTS

Figure 1:
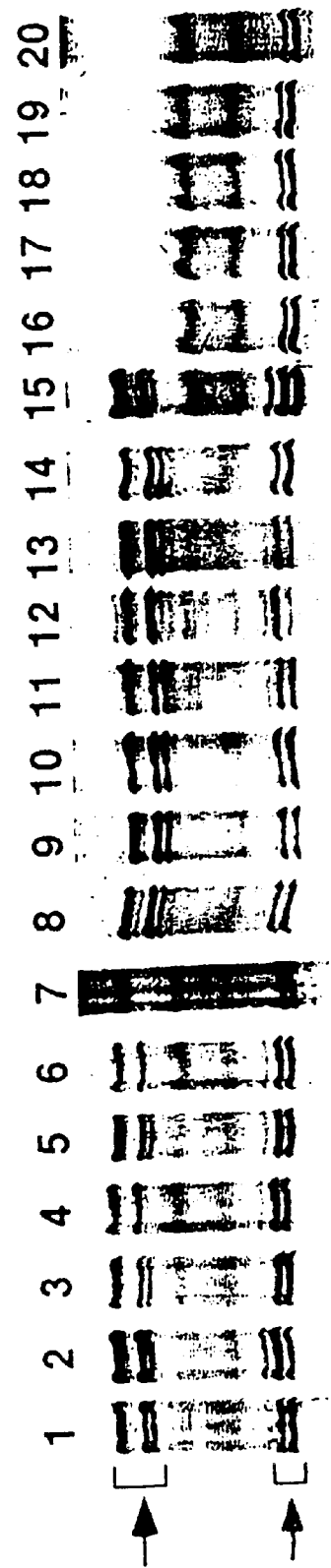
FIG. 1 shows the results of nonradioactive PCR-SSCP analysis of RET exon 11 in 15 cases of sporadic medullary thyroid carcinoma (1–15), one normal tissue (16) and four normal lymphosyte DNA (17–20)

The present inventors have shown that a deletion of nine base pairs in RET exon 11 is indicative of cancer in cells of neural crest origin, e.g. multiple endocrine neoplasia (MEN) type 2A and 2B, pheochromocytoma, enteric ganglioneuromatosis, parathyroid hyperplasia, ganglioneuromas and specially MTC. The deletion causes the loss of three codons ($Leu_{633}$-$Cys_{634}$-$Arg_{635}$) and the substitution of two ($Glu_{632}$ to Ser and $Thr_{636}$ to Ser), producing a characteristic polymerase chain reaction-based single-strand DNA conformation polymorphism (PCR-SSCP) pattern (Alemi et al., 1996, 1997). It has further been shown that this same complex deletion occurs in 14 of 15 cases of sporadic MTC, as revealed by PCR-SSCP, flourescent fragment size analysis and DNA sequencing.

By combining three different approaches (SSCP, fragment analysis and direct PCR sequencing), the identity of the nine base pair deletion (bases 1825 and 1830–7, codons 632–636, base numbering according to Takahashi et al. 1988) has been determined and it was surprisingly found to be present in practically all of the sporadic MTC tumors studied (14 of 15). Although the sensitivity of the methods differs slightly, as is evident in table 1, they complement one another by providing somewhat different types of information. PCR-SSCP is able to detect the full spectrum of genetic alterations in a give sequence, but is uninformative as to the nature of the mutation. Genescan analysis gives important information as to the exact size of the fragments, in this case demonstrating that the mutated exon 11 PCR product was 9 bp shorter than the normal allele in all positive tumors. Finally, DNA sequencing gave a definitive characterization of the mutation, which was identical in the tumors of four unrelated cases. The mutation in the proto-oncogene RET sequence was shown to have the following sequence in the region defined by position 1810 and adjacent nucleotides including position 1845 and adjacent nucleotides (base numbering according to Takahashi et al., 1988):

GAT CCA CTG TGC GAC * AGC T ******** CG GTG ATC (Seq.Id. No. 1)

wherein said sequence in normal cells is

GAT CCA CTG TGC GAC GAG CTG TGC CGC ACG GTG ATC (Seq. Id. No. 2).

It is contemplated, by the present inventors, that the deletion influences the pathological and/or cytological behaviour of the cell, e.g. enhances the cell's malignancy. Due to this, said deletion could be one causative and/or enhancing factor behind cancer. Preliminary results also show, that primers derived from the present deletion show binding affinity to DNA from patients with lymphoma. The central importance of the present deletion makes it an important target for gene therapy strategies, such as PNA based blocking methods or antisense methods.

TABLE 1

Results from PCR-SSCP, GeneScan and sequencing

| Case | Diagnosis[a] | Age (years) | Sex | PCR-SSCP | GeneScan | Sequence |
|------|-----------|-------------|-----|----------|----------|----------|
| 1 | s MTC | 58 | M | +[b] | + | + |
| 2 | " | 57 | M | + | + | + |
| 3 | " | 12 | M | + | + | |
| 4 | " | 41 | M | + | + | |
| 5 | " | 34 | F | + | + | + |
| 6 | " | 73 | F | + | + | |
| 7 | " | 37 | M | −[c] | − | − |
| 8 | " | 53 | F | + | + | |
| 9 | " | 76 | F | + | + | |
| 10 | " | 51 | M | + | + | |
| 11 | " | 67 | F | + | + | |
| 12 | " | 49 | M | + | + | + |
| 13 | " | 63 | F | + | + | |
| 14 | " | 41 | M | + | + | |
| 15 | " | 80 | M | + | + | |
| 16 | NT | 49 | M | − | − | − |
| 17 | NL | | | − | − | |
| 18 | " | | | − | − | |
| 19 | " | | | − | − | |
| 20 | " | | | − | − | |

[a]sMTC = sporadic medullary thyroid carcinoma, NT = normal thyroid, NL = normal lymphocytes.
[b]+ indicates a result suggesting presence of the 9 bp deletion.
[c]− indicates normal findings.

The identical, complex nature of the deletions found here suggests that non-random processes lead to their occurrence. This has prompted the present inventors to examine the DNA sequence in and adjacent to the deletions in search of predisposing factors. It has been demonstrated in bacterial systems that inverted repeat sequences (palindromes) are preferentially deleted spontaneously (Albertini et al., 1982; Brunier et al., 1988; DasGuta et al., 1987; Galas, 1978; Schaaper et al., 1986) while direct repeats has been implicated in the occurrence of deletions in a number of viral systems (Singer and Westly, 1988). Yamakawa-Kobayashi et al. found several inverted repeat sequences around the region of a complex nucleotide deletion-substitution in the LDL receptor gene, associated with familial hypercholesterolemia (Yamakawa-Kobayashi et al., 1993). As a generative mechanism for this complex mutation, they propose that these inverted repeat sequence formed a hairpin-loop structure during replication, and that the deletional event occurred within this structure.

Several factors in the local DNA sequence environment of small deletions (1–20 bp) linked to inherited and sporadic human diseases have been shown to correlate to the deletions, including short direct repeats (2–8 bp), inverted repeats, symmetric elements (e.g. AGTGCTGA in which loss of the C leaves a sequence symmetric about the central G) and the presence of a specific consensus sequence (TGA/GA/GG/TA/C) (Krawczak and Cooper, 1991).

Figure 4:
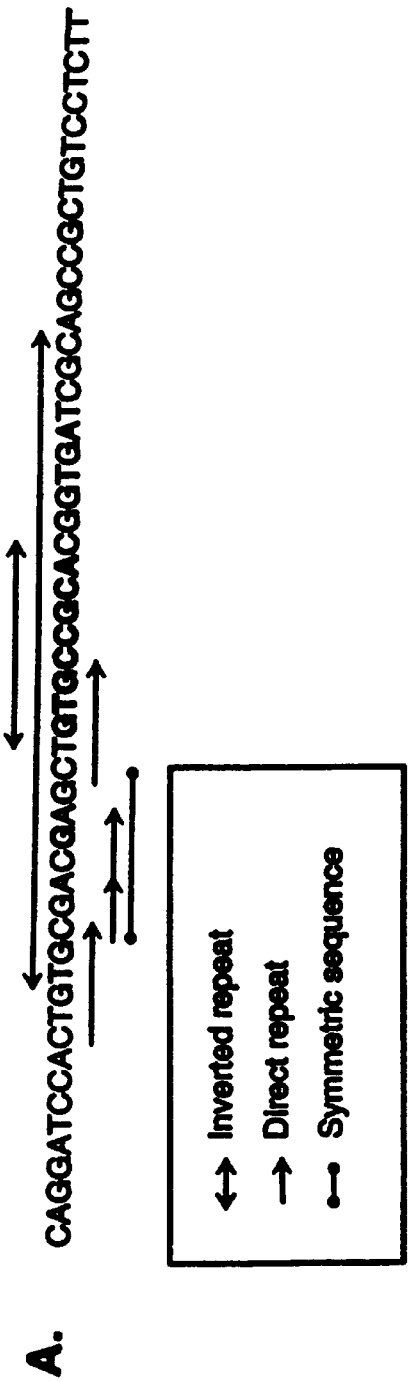
Figure 4:
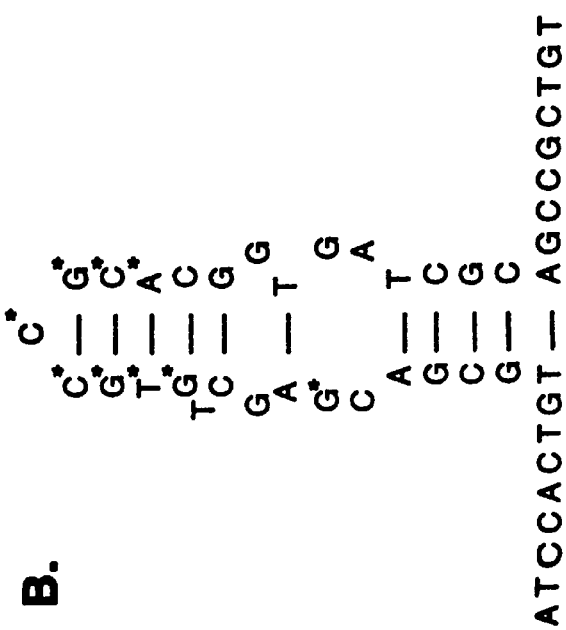

A number of these factors are also present in the vicinity of the 9 bp RET compound deletion, as demonstrated in FIG. 4A. The 8 bp deletion itself is palindromic, and is part of a larger imperfect palindrome (FIG. 4B) that could produce a hairpin-loop with relatively high thermodynamic stability under physiological conditions ($\Delta G=-13,4$ kcal/mol). The first bases of the 8 bp deletion are also part of a 6 bp direct repeat (CTGTGC), and four bases fit the six base consensus sequence (TGCCGC). The single base pair deletion at position 1825 is within the latter of two immediate direct repeats (CGA CGA), and when deleted leaves a 7 bp symmetric element (CGACAGC, FIG. 4).

Why then would both deletions be seen in such a large proportion of tumors? Either of these two deletions alone would result in a frameshift mutation with subsequent loss of RET protein function, and thus no neoplastic phenotype. However, when both occur in the same allele, the mutation would once again be in frame, allowing for the formation of mutant mRNA and protein. It has been demonstrated that non-conserved point mutation at the $Cys_{634}$ codon causes constitutive activation of the tyrosine kinase of RET, and transfection of fibroblasts with the $Cys_{634}$-mutated construct gives a transformed phenotype (Santoro et al., 1995). It is thus plausible that loss of this Cysteine codon through deletion could also result in constitutive activation and neoplasia, possibilities which are presently under investigation.

Previous studies have demonstrated several types of RET mutations in conjunction with sporadic MTC, although in most cases no abnormality has been found (Takahashi, 1995). The most commonly seen mutations alter codons 918, 883 or 768, each in a small proportion of cases (Donis-Keller, 1995; Lloyd, 1995). However, two reports have mentioned the deletion of 6 bp including codon 630 or 634, each in a single case of sporadic MTC (Donis-Keller, 1995; Kimura et al., 1995).

The nucleotide sequence or portions thereof according to the present invention is useful as DNA-primers and nucleic acid probes to diagnose the presence of cancerous and pre-cancerous cells. Such probes, in combination with suitable, conventional markers are applicable e.g. in post operative monitoring and in the tracing of metastases. DNA-primers and nucleic acid probes, based on the new sequence are also easily applicable to kits and methods for genetic screening.

This nucleotide sequence also permits the production of polypeptides which are useful as standards or reagents in diagnostic tests and/or as components of vaccines. Antibodies, both monoclonal and purified polyclonal, directed against said sequence or epitopes thereon are also useful for diagnostic tests and as therapeutic agents for passive immunization. The use of said diagnostic tests, produced with use of the inventive sequence, will enable early and sensitive detection of cancerous and pre-cancerous cells.

Another embodiment of the invention is the manufacture of a vaccine composition, including one of the steps of expressing a polypeptide with use of the inventive sequence, use of a purified protein or use of whole cells exhibiting the present deletion. A vaccine composition would have specific pregnancy in treating blood based malignancies, such as lymphoma and leukemia. The manufacture of a vaccine composition based on the invention as disclosed, requires only routine experimentation and the application of conventional techniques, available at the date of filing.

An embodiment of specific importance is the use of the information derived from the present nucleotide sequence or portions thereof to block or permanently replace said region or epitopes thereon using anti sense DNA methods or PNA based blocking methods.

Still another embodiment is the manufacture of probe based radiological or chemotherapeutical pharmaceuticals for treatment of cancer.

EXAMPLES

Formalin fixed, paraffin embedded tumors demonstrating morphological characteristics typical of MTC (15 cases) were retrieved from pathology department archives, and sporadic tumors were selected by review of the patients's clinical records. The tumor cells were stained for the C-cell markers chromogranin A and calcitonin (Boehringer Mannheim) in routine immunohistochemistry. Parallel sections from these blocks were used for DNA extraction.

Genomic DNA was isolated from one 10-$\mu$ thick section of each tumor tissue block. The sections were deparaffinizied with xylene and washed in absolute ethanol. Dried samples were treated with 500 $\mu$g/ml proteinase K in 200 $\mu$l digestion buffer (50 mM KCl, 10 mM Tris-HCl pH 8.3) at 56° C. overnight, and the enzyme was then inactivated by boiling for 10 minutes. DNA extracted from normal thyroid tissue, other thyroid tumors and normal blood lymphocytes was used as control.

Oligonucleotide primers for amplification of exon 11 of the RET proto-oncogene were chosen from previously published data (Donis-Keller et al., 1993). PCR fragments were amplified from 5 $\mu$l genomic tumor or control DNA in a 30 $\mu$l mixture containing 0.2 mM dNTP, 0,5 $\mu$M each primer, 1.5 mM Mg$^{2+}$, 50 mM KCl, 10 mM Tris-HCl pH 8,3, 0.5 U Taq DNA polymerase (Perkin Elmer). After initial denaturation at 95° C. for 1 min., annealing at 65° C. for 1 min, extension at 72° C. for 1 min. were carried out, followed by a final extension at 72° C. for 10 min. The expected size of the amplification products is 192 bp.

Example 1
1.1 PCR-SSCP Analysis

One $\mu$l aliquots of PCR-product in 1 $\mu$l of denaturing solution (0.05% bromo-phenol blue, 0.05% xylene cyanol in formamide) were heated to 95° C. for 5 minutes, followed by rapid cooling on ice. 1 $\mu$l of the denatured sample was separated using a Phast Gel system electrophoresis apparatus (Pharmacia LKB Biotechnology, Uppsala, Sweden) on premade 4–15% gradient polyacrylamide gels under non-denaturing conditions. The instrument was programmed with a pre-run at 100 Vh followed by 50 Vh at 16° C. The gels were silver stained according to the manufacturer's instructions (Pharmacia LKB, Biotechnology).

A PCR-SSCP pattern indicating the previously described 9 bp compound deletion in exon 11 was found in 14 of 15 sporadic MTC cases. Representative results of the nonradioactive PCR SSCP analysis are shown in FIG. 1. Tumor samples (lanes 1–6, 8–15) demonstrated a highly divergent heterozygous SSCP pattern as compared to a normal thyroid tissue from one patient and normal lymphocyte controls (lanes 16 and 17–20, respectively).

1.2 Fluorescent Fragment Size Analysis of PCR Product by Genescan

For automated fluorescent fragment analysis, exon 11 PCR products were generated using the primer pair described above, the forward primer labeled with (6-carboxy-2',4',7',4,7-Hexachlorofluorescence) at the 5' end. The PCR product was diluted 1:4 with distilled water and 0.5 $\mu$l was added to a mixture of 12 $\mu$l formamide and 0.5 $\mu$l molecular size standard (GS350, Applied Biosystems Inc.). The samples were denatured at 90° C. for two min and placed on ice, after which they were loaded onto a 6% polyacrylamide gel containing urea in an ABI 373A DNA sequencer (Applied Biosystems Inc.). The electrophoresis was run for 14 hours and the flourescent signals analyzed using the Gene Scan 672 software package (Applied Biosystems Inc.), which assigns DNA chain length in bases in relation to the size markers. The resolution of the method is reported by the manufacturer to be two bases.

Figure 2:
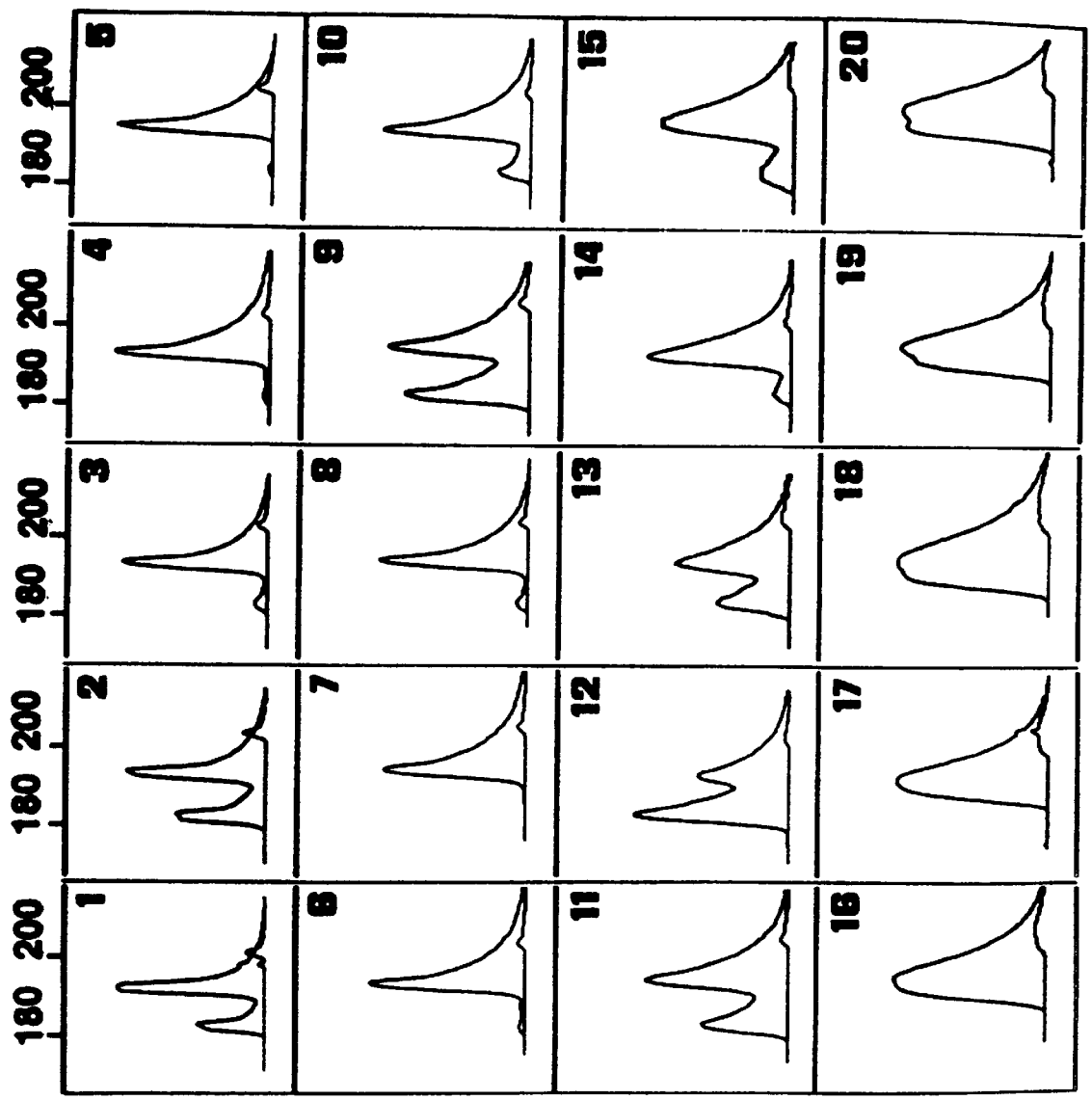
FIG. 2 shows the electrophoretic profiles of fluorescent RET proto-oncogene PCR product from 15 MTC cases (1–15), one normal thyroid tissue (16) and four lymphocyte DNA (17–20) analyzed with GeneScan on an automated sequencer.

The usefulness of this new approach was assessed using amplicons of 20 DNA samples (15 MTC tumors and five controls). Chromatograms of the Genescan analysis are shown in FIG. 2. Products derived from normal thyroid tissue gave one sharp peak of fluorescence (FIG. 2, case 16) corresponding to the normal allele at 192 bp, whereas amplicons from 14 of 15 sporadic MTC cases yielded both the normal 192 bp peak and a 9 bp shorter fragment at 183 bp (FIG. 2, 1–14 and table 1). One case of MTC and the normal lymphocyte controls showed a normal fragment pattern (FIG. 2, cases 7 and 17–20).

Example 2
Nucleotide Sequensing

Amplified exon 11 DNA was purified by electrophoretic separation on 1% agarose gels followed by ion-exchange isolation from excised bands of approximately 192 bp (Jetsorb, Genomed Inc. N.C.). The purified DNA was diluted in 100 $\mu$l of distilled water, and 8 $\mu$l was used as template. Fluorescence-based dideoxy terminator cycle sequencing was performed using a Taq polymerase based kit (Applied Biosystems Inc., Foster city) according to the manufacturer's protocol, and an automated DNA sequencer (Model 373A, Applied Biosystems Inc.). The sequence of both sense and antisense strands of the PCR products was determined.

To confirm the results of the Genescan, the present inventors then sequenced the PCR product from four randomly selected cases and one normal thyroid control. Sequencing of the sense and antisense strands of the exon 11 PCR product revealed the deletion of nine bases at positions 1825 and 1830-7 within the Cys-rich extracellular domain (FIG. 3). This alteration results in the loss of codons 633–635 (Leu-Cys Arg), including a Cys at 634 reported to show missense mutation in MEN 2A (Mulligan et al., 1993). In addition, Glu at codon 632 and Thr at 636 are both altered to Ser (FIG. 3). The sequence of the normal allele was seen as a background chromatogram nine bases out of phase, beginning at the deleted region and continuing to the end of the fragment. No exon 11 deletions were found in the patients normal tissue.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto.

References

Albertini A M, Hofer M, Calos M P and Miller J H. (1982). Cell, 29, 319–328.

Alemi, M., Lucas, S. D., Sällström, J. F., Bergholm, U. Åkerström, G. and Wilander, E., (1997), *Oncogene* 14, in press.

Alemi M, Lucas S D, Sällström J F, Åkerström G and Wilander E. (1996). Anticancer Res, 16, 2619–2622.

Bolino A, Schuffenecker I, Luo Y, Seri M, Silengo M, Tocco T, Chabrier G, Houdent, C, Murat A, Schlumberger M, Tourniaire J, Lenoir G M and Romeo, G. (1995). Oncogene, 10, 2415–2419.

Brunier D, Michel B and Ehrlich S D. (1988). Cell, 52, 883–892.

Carney J A, Sizemore G W and Lovestedt S A. (1976). Oral Surg Oral Med Oral Pathol, 41, 739–752.

DasGupta U, Weston H K and Berg D E. (1987). Genetics, 115, 41–49.

Donis-Keller H. (1995). J Inter. Med., 238, 319–325.

Donis-Keller H, Dou S, Chi D, Carlson K M, Toshima K, Lairmore T C, Howe, J R, Moley J F, Goodfellow P and Wells S J. (1993). Hum Mol Genet, 2, 851–856.

Durbec P, Marcos-Gutierrez C V, Kilkenny C, Grigoriou M, Wartiowaara K, Suvanto P, Smith D, Ponder B, Constantini F, Saamra M, Sariola H and Pachnis V. (1996). Nature, 381, 789–793.

Eng C, Smith D P, Mulligan L M, Healey C S, Zvelebil M J, Stonehouse T J, Ponder M A, Jackson C E, Waterfield M D and Ponder B A. (1995). Oncogene, 10, 509–513.

Farndon J R, Leight G S, Dilley W G, Baylin S B, Smallridge R C, Harrison T S and Wells S A. (1986). Br J Surg, 73, 278–281.

Mulligan L M, Kwok J B, Healey C S, Elsdon M J, Eng C, Gardner E, Love D R, Mole S E, Moore J K, Papi L, Ponder M A, Telenius H, Tunnacliffe A and Ponder B A J. (1993). Nature, 363, 458–460.

Santoro M, Carlomagno F, Romano A, Bottaro D P, Dathan N A, Grieco M, Fusco A, Vecchio G, Matoskova B, Kraus M H and Di Fiore P P. (1995). Science, 267, 381–383.

Schaaper R M, Danforth B N and Glickman B W. (1986). J Mol Biol, 189, 272–284.

Schimke R N, Hartmann W H, Prou T E and Rimoin D L. (1968). N Eng J Med, 279, 1–7.

Schuffenecker I, Billaud M, Calender A, Chambe B, Ginet N, Calmettes C, Modigliani E and Lenoir G M. (1994). Hum Mol Genet, 3, 1939–1943.

Singer B S and Westly J. (1988). J Mol Biol, 202, 233–243.

Sipple J H. (1961). Am J Med, 31, 163–166.

Takahashi M. (1995). Crit Rev Oncog, 6, 35–46.

Takahashi M, Buma Y, Iwamoto T, Inaguma Y, Ikeda H and Hiai H. (1988). Oncogene, 3, 571–578.

Trupp M, Arenas E, Fainzilber M, Nilsson A S, Sieber B A, Grigoriou M, Kilkenny C, Salazar-grueso E, Pachnis V, Arumae U, Sariola H, Saamra M and Ibanez C F. (1996). Nature, 381, 785–789.

Yamakawa-Kobayashi K, Kobayashi T, Yanagi H, Shimakura Y, Satoh J and Hamaguchi H. (1993). Human Genetics, 93, 625–628.

---

SEQUENCE LISTING

<160> NUMBER OF SEQ ID NOS: 2

<210> SEQ ID NO 1
<211> LENGTH: 27
<212> TYPE: DNA
<213> ORGANISM: Homo sapiens

<400> SEQUENCE: 1
gatccactgt gcgacagctc ggtgatc                27

<210> SEQ ID NO 2
<211> LENGTH: 36
<212> TYPE: DNA
<213> ORGANISM: Homo sapiens

<400> SEQUENCE: 2
catccactgt gcgacgagct gtgccgcacg gtgatc                36

---

Galas D J. (1978). J Mol Biol, 126, 858–863.

Hofstra R M, Landsvater R M, Ceccherini I, Stulp R P, Stelwagen T, Luo Y, Pasini B, Höppener J W, Ploos van Amstel H K, Romeo G, Lips C J M and Buys C H C M. (1994). Nature, 367, 375–376.

Jackson C E and Norum R A. (1989). Henry Ford Hosp Med J, 37, 116–119.

Jing S, Wen D, Yu Y, Holst P L, Luo Y, Fang M, Tamir R, Antonio L, Hu Z, Cupples R, Louis J C, Hu S, Altrock B W and Fox G M. (1996). Cell, 85, 1113–1124.

Kimura T, Yoshimoto K, Yokogoshi Y and Saito S. (1995). Endocr J, 42, 517–525.

Krawczak M and Cooper D N. (1991). Human genetics, 86, 425–441.

Lairmore T C and Wells S J. (1993). Br J Surg, 80, 1092–1093.

Lloyd R V. (1995). Am J Pathol, 147, 1539–1544.

What is claimed is:

1. An isolated and purified nucleic acid comprising a nucleotide sequence which consists of GAT CCA CTG TGC GAC AGC TCG GTG ATC (SEQ ID NO: 1).

2. A method for use in the diagnosis of human cancer, comprising the step wherein the occurrence or absence of a nucleotide sequence comprising SEQ. ID. NO: 1 of claim 1 is determined in samples, taken from the human body, whereby presence of said sequence is taken as an indication of cancer.

3. A method for use in the diagnosis of human cancer, comprising the step wherein the occurrence or absence of a nucleotide sequence comprising SEQ ID NO: 1 of claim 1 is determined in samples, taken from the human body, whereby presence of said sequence is taken as an indication of cancer in cells of neural crest origin.

4. A method for use in the diagnosis of human cancer, comprising the step wherein the occurrence or absence of a nucleotide sequence comprising SEQ ID NO: 1 of claim 1 is determined in samples, taken from the human body, whereby presence of said sequence is taken as an indication of a precancerous condition.

5. A method for use in the diagnosis of human cancer, comprising the step wherein the occurrence or absence of a nucleotide sequence comprising SEQ ID NO: 1 of claim 1 is determined in samples, taken from the human body, whereby presence of said sequence is taken as an indication of a precancerous condition in cells of neural crest origin.

6. A method according to claim 2 wherein said samples are subjected to a treatment, selected from the group consisting of DNA amplification, RNA amplification, DNA ligation, PCR, DNA-sequencing, RNA-sequencing, nucleic acid hybridization, electrophoresis, or a combination thereof.

7. A method for the postoperative monitoring of the recurrence or metastasis of human cancer wherein said method comprises using a DNA oligonucleotide to detect the presence of SEQ ID NO: 1 in a sample taken from a patient who has undergone a cancer operation, wherein the presence of SEQ ID NO: 1 indicates a recurrence or metastasis.

8. A method for genetic screening for a predisposition or occurrence of human cancer caused by a deletion in the proto-oncogene RET which results in the presence of SEQ ID NO: 1 in a sample, wherein said method comprises detecting the presence of SEQ ID NO: 1 in a sample wherein said detecting comprises using DNA probes in a hybridization assay and/or using nucleic acid primers in an amplification assay wherein the presence of SEQ ID NO: 1 indicates a predisposition or occurrence of cancer.

\* \* \* \* \*